United States Patent
Camus et al.

(10) Patent No.: US 8,386,019 B2
(45) Date of Patent: Feb. 26, 2013

(54) ARRANGEMENT FOR SUPPORTING A PERCUTANEOUS INTERVENTION

(75) Inventors: Estelle Camus, Mountain View, CA (US); Oliver Meissner, München (DE); Martin Ostermeier, Buckenhof (DE); Thomas Redel, Poxdorf (DE)

(73) Assignee: Siemens Aktiengesellschaft, München (DE)

( * ) Notice: Subject to any disclaimer, the term of this patent is extended or adjusted under 35 U.S.C. 154(b) by 779 days.

(21) Appl. No.: 12/070,885

(22) Filed: Feb. 21, 2008

(65) Prior Publication Data

US 2008/0208212 A1      Aug. 28, 2008

(30) Foreign Application Priority Data

Feb. 23, 2007   (DE) .................. 10 2007 009 017

(51) Int. Cl.
    *A61B 5/05*      (2006.01)
(52) U.S. Cl. ......... 600/424; 600/407; 600/411; 600/427
(58) Field of Classification Search .................. 600/407, 600/411, 424, 427; 378/42; 702/94, 150; 606/130

See application file for complete search history.

(56) References Cited

U.S. PATENT DOCUMENTS

| | | | | |
|---|---|---|---|---|
| 7,542,791 B2 * | 6/2009 | Mire et al. | ..................... | 600/407 |
| 7,567,834 B2 * | 7/2009 | Clayton et al. | ................. | 600/424 |
| 7,697,972 B2 * | 4/2010 | Verard et al. | ................... | 600/424 |
| 7,751,865 B2 * | 7/2010 | Jascob et al. | ................... | 600/424 |
| 7,822,466 B2 * | 10/2010 | Stoianovici et al. | .......... | 600/427 |
| 7,835,778 B2 * | 11/2010 | Foley et al. | ..................... | 600/407 |
| 7,835,784 B2 * | 11/2010 | Mire et al. | ..................... | 600/424 |
| 7,840,253 B2 * | 11/2010 | Tremblay et al. | ............. | 600/424 |
| 2007/0244386 A1 | 10/2007 | Steckner et al. | | |
| 2008/0177280 A1 * | 7/2008 | Adler et al. | ..................... | 606/130 |
| 2008/0281181 A1 * | 11/2008 | Manzione et al. | ............ | 600/407 |
| 2009/0149867 A1 * | 6/2009 | Glozman et al. | ............... | 606/130 |

FOREIGN PATENT DOCUMENTS

WO     WO 2005/030330 A1     4/2005

* cited by examiner

*Primary Examiner* — Tse Chen
*Assistant Examiner* — Baisakhi Roy

(57) ABSTRACT

The invention relates to an arrangement for assisting a percutaneous intervention, comprising an imaging system for tomographic imaging, a robot registered therewith and devices for capturing movements of the patient. A processing unit registers a 4D image dataset recorded before the intervention with a 2D or 3D image dataset of the patient which was recorded immediately before the intervention by the imaging system at a defined respiratory position. From this image data, the access path is transmitted to the robot as a function of the movements captured during recording the 4D image dataset and registration, said robot in turn, depending on the instantaneous movement data, holding the instrument on a predetermined target path and preventing the instrument from being advanced by the person if and as long as the instantaneous movement data does not match the previously recorded movement data. The arrangement reduces the risk of puncture errors.

13 Claims, 2 Drawing Sheets

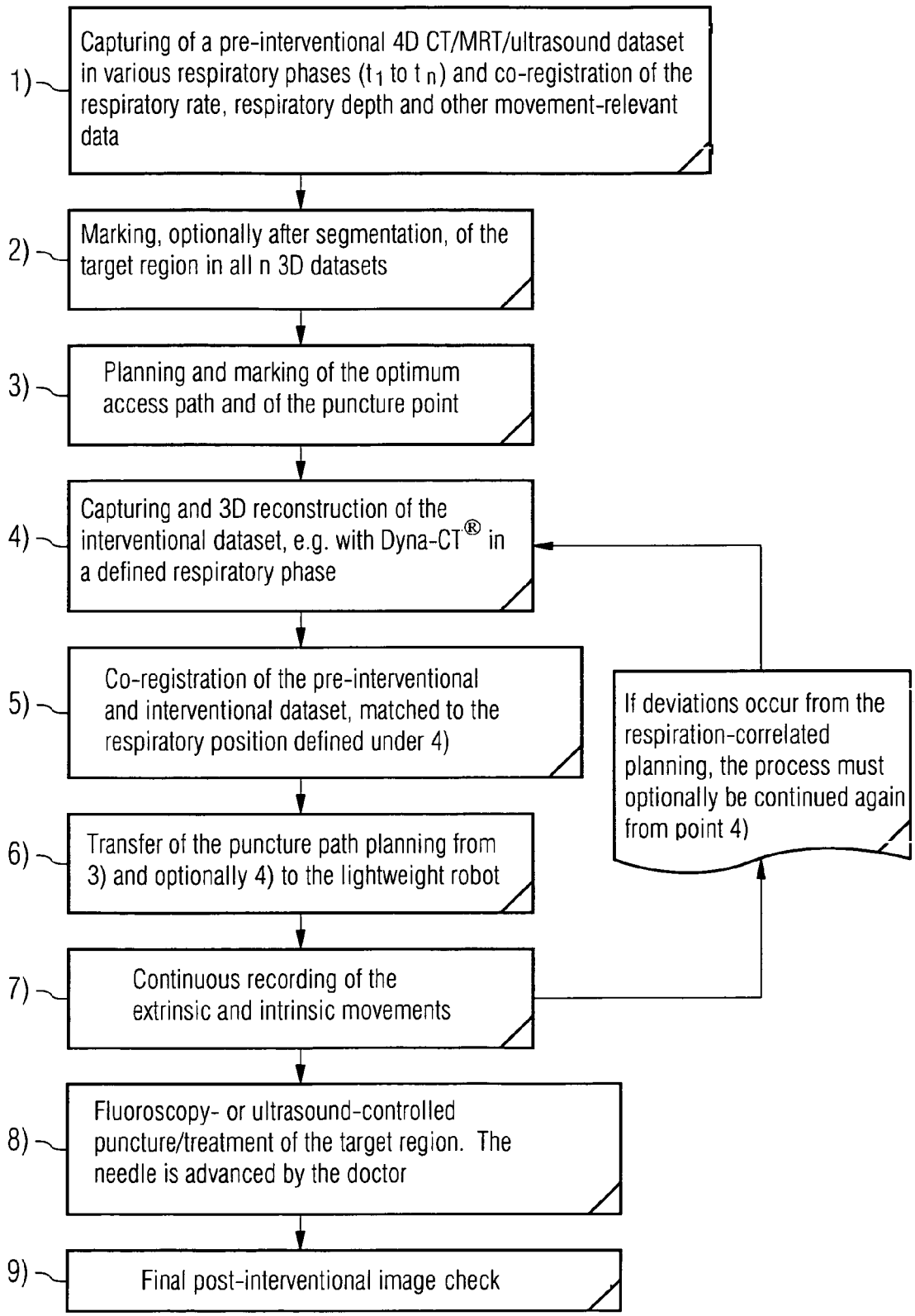

ARRANGEMENT FOR SUPPORTING A PERCUTANEOUS INTERVENTION

CROSS REFERENCE TO RELATED APPLICATIONS

This application claims priority of German application No. 10 2007 009 017.1 filed Feb. 23, 2007, which is incorporated by reference herein in its entirety.

FIELD OF THE INVENTION

The present invention relates to an arrangement for supporting a percutaneous intervention, comprising inter alia an imaging system for three-dimensional tomographic imaging, in particular a C-arm x-ray system.

BACKGROUND OF THE INVENTION

Percutaneous methods play an important role in the diagnosis and treatment of different diseases. They are based upon the principle of puncturing a pathological process through the skin. By this means, for example, tissue samples can be removed for diagnostic purposes using special biopsy needles. A treatment can also be carried out with the aid of a puncture, for example the drainage of an abscess or the thermoablation of a solitary liver metastasis. The percutaneous puncture is generally performed after a preceding imaging diagnosis by means of computer tomography (CT), magnetic resonance tomography (MRT) or ultrasound. The intervention itself can be monitored by means of imaging in real time and controlled with the aid of imaging, with CT or ultrasound currently being the imaging methods predominantly used.

Due to the minimally invasive nature, the safe access paths and the opportunities for local treatment, it is expected that percutaneous interventions will continue to increase in the next few years. Through improved diagnostics, potential pathologies can be captured at ever earlier stages and ever smaller lesions can be punctured in difficult-to-access positions, for example unclear coin-shaped lesions in the lung with dimensions between 10 and 20 mm. Percutaneous diagnostics and treatment do, however, also have some limitations. A complication rate of between 3.9% and 23.9% is reported in the literature, though the complications concerned are predominantly non-life-threatening hemorrhages, hematomas, pneumothoraces or organ injuries. Nonetheless, there is also the risk of dying from such an intervention, particularly in the event of inadvertent damage to a large vessel. A serious problem here is that of a puncture error. The rate of incorrect or incomplete punctures is reported in the literature as being up to 30%. Puncture errors can lead to a false-negative diagnosis or be the cause of an inadequate treatment dose in the desired target region. The number of puncture errors must be kept as low as possible, both in the interest of the patient and from the point of view of efficient and cost-saving medicine.

The difficulty of precise puncture lies in the variability of the target region as a result of respiratory movements, pulse-synchronous movements of organ and target region or lesion, also relative to one another, as well as possible unpredictable movements of the patient, for example caused by pain stimuli during the intervention.

Some problems can be traced to the fact that, after looking through the image recordings from the preceding imaging diagnosis and planning a suitable access path, radiologists frequently perform punctures intuitively, i.e. as a "blind puncture". The variation in the position of a lesion as a result of respiratory activity or pulsating organ movements is estimated and included in the planning of the puncture. However, considerable scope for movement remains which almost routinely and depending also on the experience of the person performing the intervention leads to multiple puncture attempts and repeated position checks. The puncture procedure, primarily in specialized centers, is optionally monitored in real time, for example by means of x-ray or ultrasound imaging.

WO 2005/030330 A1 describes an arrangement for radiation treatment which can also be used to assist a percutaneous intervention, with an instrument being guided by a robot. To capture movements of the target region, a 4D image dataset is firstly recorded by means of markers attached to the patient externally. The target region is then marked in the individual images of the 4D image dataset so that an allocation table between the position of the externally attached markers and that of the target region located internally can finally be computed. During the intervention, the markers lying externally, and thus the patient's movements, are captured via a tracking system. By means of the allocation table, the position of the target area is determined as a function of the movement status in order in this way to be able to align the treatment instrument to the target area with greater precision.

SUMMARY OF THE INVENTION

The object of the present invention is to indicate an arrangement for assisting a percutaneous intervention, which arrangement reduces the risk of puncture errors.

The object is achieved in the arrangement as claimed in the independent claim. Advantageous embodiments of the arrangement are the subject matter of the subclaims or can be inferred from the description below and the exemplary embodiment.

An exemplary arrangement comprises at least one imaging system for two-dimensional or three-dimensional tomographic imaging, preferably a C-arm x-ray system, a robot which is registered with the imaging system and is equipped with a mounting unit for mounting an instrument for the percutaneous intervention, one or more devices for capturing external and/or internal movements of a patient supported on a supporting device and a specially configured processing unit. In this way, the movements which can be captured with the device comprise at least the respiratory movement of the patient. The processing unit has various modules and an input interface. The input interface allows the 4D image dataset recorded before the intervention to be supplied, said 4D image dataset comprising a temporal sequence of 3D images of the area of the patient relevant to the intervention, to which information relating to external and/or internal movements of the patient which is recorded simultaneously is allocated in each instance and in which an access path for the percutaneous intervention is or can be marked in each instance. The 4D image dataset recorded before the intervention can also be an image dataset which was recorded in the same examination or session as the intervention, in particular by means of the imaging device of the arrangement before the start of the intervention. The registration module is configured such that it registers the 4D image dataset recorded before the intervention with a 2D or 3D image dataset of the patient, which was recorded by means of the imaging system immediately before the intervention at a defined respiratory position of the patient. The 3D image dataset may, in cases in which the 4D image dataset was recorded in the same examination by means of the same imaging device, also be 3D image data from the 4D image dataset. On the basis of the registration carried out with the registration module, the generation module generates data for the robot from the access paths in the 3D images data, said data predetermining for the robot a target path for the instrument, said path varying with the external and internal movements recorded. The control program for the robot is executed here such that during the intervention the robot holds the instrument, which is guided by a person performing the intervention, as a function of instantaneous patient movement data which is transmitted to the control of the robot by the one or more devices for capturing external and/or internal movements during the intervention, on the predetermined target path and prevents the instrument from being advanced if and as long as a deviation of the movements captured during the intervention from the movements recorded with the 4D image dataset exceeds a predeterminable limit value.

In this way, when this arrangement is used, internal and/or external movements of the patient during the intervention are automatically taken into account in guiding the instrument so that the risk of puncture errors due to such movements is reduced. The robot ensures that the person performing the intervention always guides the instrument in every movement phase (internal and/or external movements) of the patient on the path predefined for this movement phase. If movements are captured which did not occur in the preliminary examination during the recording of the 4D image dataset, on the basis of which the access was planned, then the robot prevents the instrument from being advanced further by the person performing the intervention.

The robot used here is preferably a 6-DOF (degrees of freedom) or a 7-DOF robot. In the preferred embodiment, a so-called lightweight robot is used, which preferably has a modular structure and is modeled on the human arm. Robots of this type have seven degrees of freedom and, in comparison to the classic industrial robots provide greater flexibility and ease of manipulation. An integrated sensor system, in conjunction with innovative control algorithms, enables it to yield to external forces and to perform complex movement sequences. A lightweight robot can also be "taught" job steps by being taken by the hand and guided. No time-consuming programming is required for this.

The one or more devices for capturing external and/or internal movements preferably also comprise, in addition to a device for recording respiratory movement, an ECG system for capturing the heartbeat. Other devices for capturing external and/or internal movements, for example a position capturing system for external movements, can also be deployed. These may, for example, be an optical system with a camera which captures markers attached to the patient in the area of the intervention and movements of said markers. Here, it is necessary for the movements recorded in drawing up the pre-interventional 4D image dataset also to be capturable by means of the devices of the arrangement.

The proposed arrangement thus uses a combination of motion-adapted 4D-imaging and a robot system in order, on the one hand, automatically to take cyclical movements such as respiration or pulse beat into account during the intervention and, on the other hand, to capture involuntary movements of the patient during the intervention and to protect the patient appropriately. The facility which allows the person performing the treatment certain movements in guiding the instrument while blocking others, enables a puncture to be carried out in a highly precise manner.

BRIEF DESCRIPTION OF THE DRAWINGS

The proposed arrangement is explained again briefly below with reference to an exemplary embodiment in conjunction with the drawings, in which:

FIG. 1 shows a highly schematized exemplary representation of the proposed arrangement and FIG. 2 shows an example of the performance of a percutaneous intervention using the proposed arrangement.

DETAILED DESCRIPTION OF THE INVENTION

Figure 1:
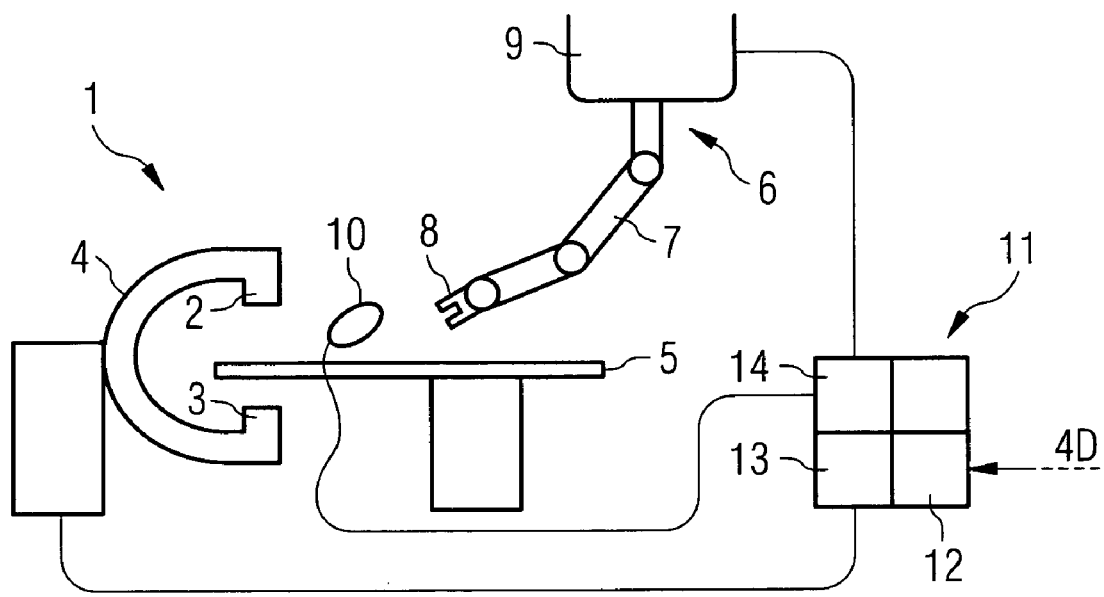

In the schematic representation in FIG. 1, a C-arm x-ray device 1 is indicated as an imaging system, comprising inter alia the C-arm 4 with the x-ray recording system, consisting of x-ray tube 2 and x-ray detector 3, mounted thereon and the patient supporting device 5. The imaging system can also be other systems, such as for example an ultrasound device, a computer tomograph or a functional imaging device, in particular for positron emission tomography.

In the present case, a robot 6, which at the end of its robot arm 7 carries the mounting device 8 for a puncture needle, is mounted on the ceiling. In the present example, only one device for capturing internal and/or external movements of the patient is shown as a respiratory belt 10. The C-arm x-ray system 1, the control 9 of the robot 6 and the respiratory belt 10 are connected to a processing unit 11. This processing unit has an input interface 12 for feeding a pre-operatively recorded 4D image dataset, a registration module 13 for registering this 4D image dataset with a 3D image dataset, recorded by means of the C-arm x-ray system 1, of the patient in a defined respiratory position and the generation module 14, which generates the data for the instrument target path and transmits it for the movement and control of the robot arm 7 to the control program of the control 9 of the robot 6.

The processing of the data and control of the robot, i.e. the modules of the processing unit and the control, can in the proposed arrangement in a manner obvious to one skilled in the art also be combined in one single unit or divided between several spatially separated units. This is irrelevant to the functioning of the arrangement according to the invention.

When carrying out a percutaneous intervention using the proposed arrangement, the following method steps 1) to 9), which are also represented in the flow diagram in FIG. 2, are carried out.

1) Firstly, a pre-interventional 4D image dataset of the patient is captured and optionally reconstructed. The capturing of this image dataset can be carried out using different tomographic imaging techniques, for example by means of CT, by means of MRT or by means of ultrasound. The capturing of the image dataset takes place in various respiratory phases ($t_1$ to $t_n$), but at least in a maximum inspiration and expiration phase. Intermediate stages of respiration can optionally be interpolated. In parallel with this, the respiratory rate and depth as well as, if possible, all movement-relevant data, such as for example cardiac activity (ECG), intestinal activity or external patient movement, are recorded. Known devices, such as for example a respiratory belt system or an ECG device, can be used for this purpose. The recorded movement data is co-registered with the 4D image dataset so that a 3D image (or 3D image dataset) of the 4D image dataset can be assigned to each movement phase or vice versa.

2) In the next step, the target region is marked by the user in all the 3D images of the 4D image dataset, optionally after segmentation of the area of interest. Similarly to the following step, this can be carried out on the screen with the aid of a suitable graphic input device.

3) The optimum access path to the target region and the puncture point are then planned and marked in all n 3D images. This is carried out optionally taking into account respiratory movement, pulse-synchronous organ movement and the elasticity/deformability of the tissue in the target region and on the puncture path.

After these preparatory steps, an access path is thus established for each movement phase and is marked in the corresponding 3D images.

The recording of the 4D image dataset and the corresponding preparatory steps can also be undertaken in the larger time interval before the actual intervention.

4) Immediately before the intervention, an interventional 3D image dataset is captured by means of the C-arm x-ray system at a defined respiratory position, e.g. resting end-respiratory position, of the patient. Following 3D reconstruction of the dataset, a check of the planning and marking of the optimum access path and of the puncture point can optionally be carried out once again.

5) In the next step, registration of the pre-interventional and of the interventional dataset takes place, adapted to the respiratory position defined for generating of the interventional dataset. In this way, the deflections of the respiratory excursions and organ movements of the pre-interventional 4D image dataset can be transferred to the static interventional 3D image dataset or adapted to an altered respiratory cycle.

6) The access planning from the preceding steps is then transferred to the robot deployed. This is carried out by the generation module of the processing unit.

7) Finally, the extrinsic and intrinsic movements of the patient are continuously recorded during the intervention, for example by means of the respiratory belt system or by way of an ECG signal. The planning allows the robot to automatically follow the puncture path in a respiration-registered manner which connects the optimum access point to the variable position of the region to be punctured. Control of the robot, a lightweight robot, is programmed such that the robot only allows the puncture needle to be advanced as long as the orientation on the lightweight robot matches the respiration-correlated planning, and the movement pattern (e.g. respiratory pattern) is not abandoned. A deviation may occur for example as a result of the patient coughing. In the event of fairly long or large deviations occurring, steps 4) to 6) optionally have to be carried out again.

8) During the intervention, i.e. the puncture or treatment of the target region, the needle is advanced by the doctor. This can if necessary also be monitored by means of fluoroscopy or ultrasound imaging.

9) Finally, the doctor performs a post-interventional image check, for example with the C-arm x-ray system or an ultrasound system.

The advantage of the proposed arrangement lies in the combination of imaging which takes respiratory activity, pulse-synchronous organ movement and/or random other movements (for example, intestinal activity or patient movement) into account, with a robot system which, with the aid of this image and movement data, can assist the doctor in performing the puncture in a highly precise manner.

The invention claimed is:

1. A medical device for performing a percutaneous intervention for a patient, comprising:
   an imaging device;
   a robot that is registered with the imaging device;
   a mounting unit arranged in the robot that mounts an instrument for the intervention;
   a monitor that captures a movement of the patient and simultaneously transmits data of the movement to the robot; and
   a processing unit that:
      receives a 4D image dataset recorded before the intervention that comprises a temporal sequence of 3D images of an area of the patient each assigned a simultaneously recorded movement of the patient;
      registers the 4D image dataset with an image dataset of the patient recorded by the imaging device immediately before the intervention at a defined movement position of the patient, and
      generates a predetermined target path for the instrument as a function of the movement of the patient based on the registration,
   wherein the robot stops inserting the instrument if a deviation between the movements of the patient captured during the intervention and recorded with the 4D image dataset exceeds a predetermined limit value, and
   wherein the robot holds the instrument and is guided by a person performing the intervention in one movement while blocking other movements to perform a precise puncture.

2. A method for performing a percutaneous intervention for a patient monitored by an imaging device, comprising:
   mounting an instrument for the intervention in a robot;
   registering the robot with the imaging device;
   capturing a movement of the patient;
   simultaneously transmitting data of the movement of the patient to the robot;
   providing a 4D image dataset recorded before the intervention comprising a temporal sequence of 3D images of the patient each assigned a simultaneously recorded movement of the patient;
   registering the 4D image dataset with an image dataset of the patient recorded by the imaging device immediately before the intervention at a defined movement position of the patient; and
   generating a predetermined target path for the instrument as a function of the movement of the patient based on the registration,
   wherein the robot stops inserting the instrument if a deviation between the movements of the patient captured during the intervention and recorded with the 4D image dataset exceeds a predetermined limit value.

3. The method as claimed in claim 2, wherein the robot holds the instrument along the predetermined target path during the intervention based on the data of the movement.

4. The method as claimed in claim 2, wherein the robot is guided by a person performing the intervention.

5. The method as claimed in claim 2, wherein the robot is a lightweight robot.

6. The method as claimed in claim 2, wherein the robot has a six degrees of freedom or seven degrees of freedom.

7. The method as claimed in claim 2, wherein the imaging device is selected from the group consisting of: a C-arm x-ray system, an ultrasound device, and a computer tomography.

8. The method as claimed in claim 2, wherein the monitor comprises a respiration belt that captures a respiration movement of the patient.

9. The method as claimed in claim 2, wherein the monitor comprises an ECG system that captures a heartbeat movement of the patient.

10. The method as claimed in claim 2, wherein the monitor comprises a position capturing system that captures an external movement of the patient.

11. The method as claimed in claim 2, wherein access paths for the instrument are marked on the 3D images.

12. The method as claimed in claim 11, wherein the target path is generated from the access paths marked on the 3D images.

13. The method as claimed in claim 2, wherein the robot is mounted on a ceiling.

* * * * *